(12) United States Patent
Luigi

(10) Patent No.: US 6,669,695 B2
(45) Date of Patent: Dec. 30, 2003

(54) MULTIFUNCTIONAL ELECTROSURGICAL INSTRUMENT

(76) Inventor: Giancarlo Luigi, 162 San Rafael Ave., Reparto López, Aguadilla, PR (US) 00603

( * ) Notice: Subject to any disclaimer, the term of this patent is extended or adjusted under 35 U.S.C. 154(b) by 0 days.

(21) Appl. No.: 10/047,867

(22) Filed: Jan. 15, 2002

(65) Prior Publication Data

US 2003/0135208 A1 Jul. 17, 2003

(51) Int. Cl.[7] .............................................. A61B 18/18
(52) U.S. Cl. ........................................ 606/49; 606/41
(58) Field of Search ............................ 606/41, 42, 43, 606/44, 45, 46, 47, 48, 49, 50

(56) References Cited

U.S. PATENT DOCUMENTS

| | | | | |
|---|---|---|---|---|
| 3,974,833 A | * | 8/1976 | Durden, III | |
| 4,686,981 A | * | 8/1987 | Forintos | 128/303.17 |
| 4,932,952 A | * | 6/1990 | Wojciechowicz, Jr. | 606/49 |
| 5,180,363 A | * | 1/1993 | Idemoto et al. | 202/32 |
| 5,195,959 A | * | 3/1993 | Smith | 604/34 |
| 5,354,291 A | * | 10/1994 | Bales et al. | 604/35 |
| 5,520,685 A | * | 5/1996 | Wojciechowicz | 606/49 |
| 5,904,681 A | * | 5/1999 | West, Jr. | 606/41 |
| 5,922,003 A | * | 7/1999 | Anctil et al. | 606/170 |
| 5,980,518 A | * | 11/1999 | Carr et al. | 606/45 |

* cited by examiner

Primary Examiner—Michael Peffley
Assistant Examiner—Aaron Roane
(74) Attorney, Agent, or Firm—Eugenio J. Torres

(57) ABSTRACT

A multifunctional electrosurgical instrument for performing various oropharyngeal operative procedures comprises a serrated chisel tip for various dissecting methods; an electrocauterizer, for coagulation of blood vessels or for use as a particular dissection method; a variable speed suctioning feature to remove undesired blood in the surgical area, or to serve as irrigation source; and an irrigation feature, for ease in the identification of blood vessels and for removal of dangerous blood clots from the surgical area.

10 Claims, 1 Drawing Sheet

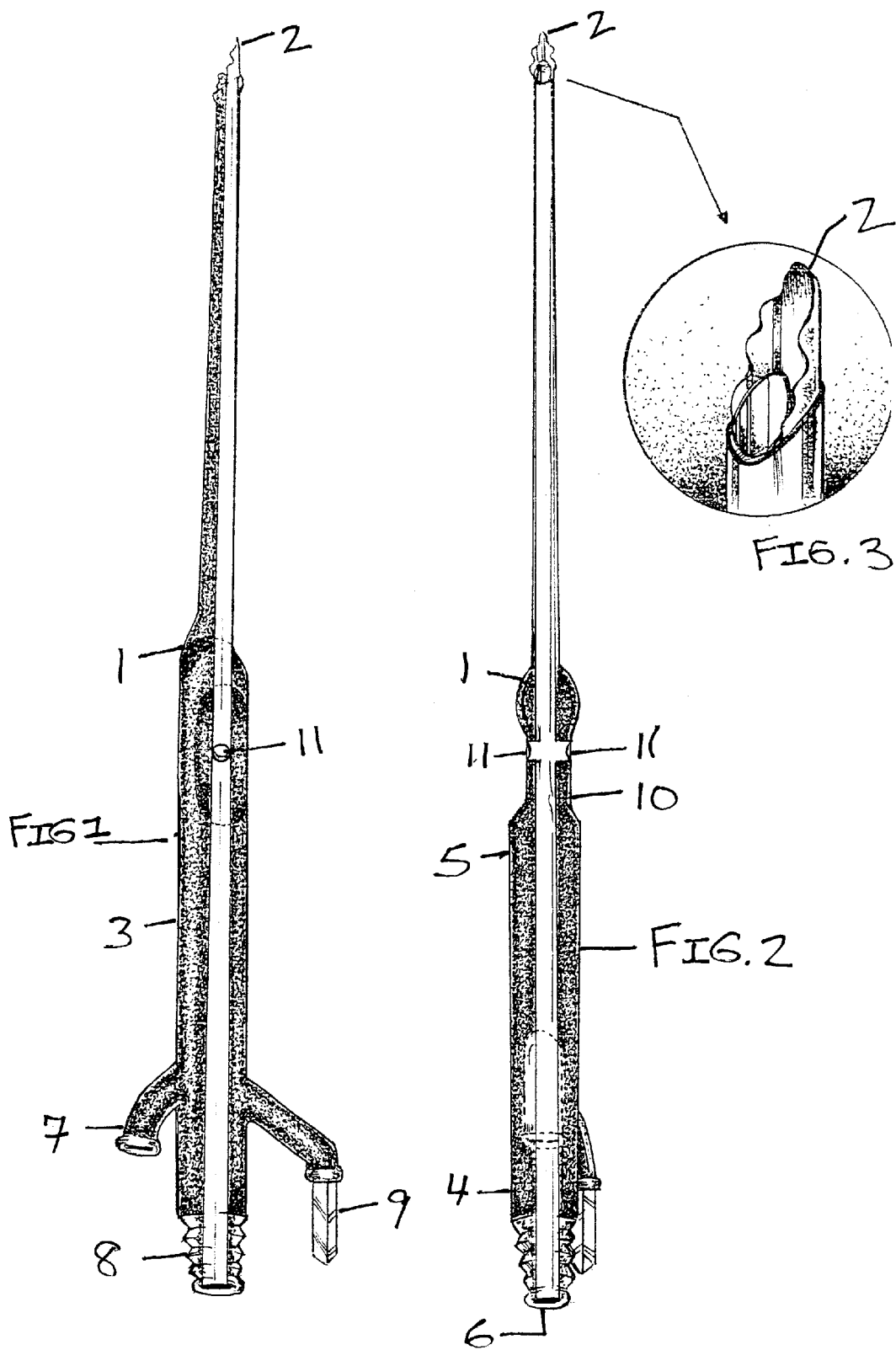

MULTIFUNCTIONAL ELECTROSURGICAL INSTRUMENT

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The present invention relates generally to surgical procedures and instruments and, more particularly, to a multifunctional electrosurgical instrument primarily intended for oropharyngeal surgical procedures having a serrated chisel tip at its distal end for sharp or cutting dissection, an electrocauterizer for coagulation of blood vessels or cutting dissection, suction features in the serrated chisel tip for removal of blood or irrigation solution from the surgical field, irrigation feature to move blood clots from the surgical field and to make easier the identification of bleeding blood vessels.

2. Discussion of the Background

The oropharyngeal cavity is heavily irrigated by blood vessels such as arteries and capillaries. It is therefore not surprising that one of the main problems during surgical procedures in that area is controlling bleeding. Surgeons generally employ electrosurgical tools to cut tissue and to coagulate bleeding blood vessels in a process known as cautery.

Electrically powered instruments such as coagulation forceps, suction cauteries, electrode cautery tips and blade electrodes are well known in the prior art. Such medical instruments are used in procedures that involve cutting and other contact with flesh or tissue. For instance, surgical blade electrodes are utilized to reduce bleeding by cauterizing the exposed tissue. Typically, a blade electrode is affixed to a handpiece activated for passing electrical energy into the blade electrode to transmit radio-frequency electrical energy to the flesh or tissue to cauterize the site. Other electrosurgical devices are similarly designed.

In order to keep the operation site visible, continuous suction devices are used to suction away blood and other debris before they accumulate and to remove smoke that is generated by the electrical cautery process. This suction is vital so that the surgeon's view of the operation site remains unobstructed and the operation can proceed safely. It is also necessary to effectively use a variety of probes to administer medicaments or to irrigate the oropharyngeal area, as necessary.

Previously, separate tools were necessary to perform the cautery, suctioning, dissecting, and irrigating. Unfortunately, if a surgeon uses several tools simultaneously, both hands are occupied and that tends to increase the difficulty of the procedure. Use of a separate suctioning device also makes precise positioning of the electrosurgical tool more difficult. To effectively use all these devices simultaneously, it is often necessary for an assistant to aid in the operation.

There are tools in the prior art which use different control schemes for controlling suction while simultaneously operating the cutting and coagulation parts of the tool. In several of these tools, suction must operate continuously as the suction force is also used to control whether the cutting or coagulation function of the tool is selected. This is achieved by the covering or uncovering of various open ports on the body of the tool by the fingers of the user to select a cutting or coagulation mode.

One particular problem with this arrangement is that it is difficult to control the pressure of suction. Some of the advantages of the present invention over the prior art are that by having open orifices at the fingertips, the surgeon can control the pressure of suction which improves the effectiveness of the cutting and coagulation functions.

Therefore, it can be appreciated that there exists a continuing need for a new and improved multifunctional electrosurgical instrument which can be used for performing oropharyngeal surgical procedures. In this regard, the present invention substantially fulfills this need.

SUMMARY OF THE INVENTION

It is an object of the present invention to provide an instrument that provides pinpoint electrosurgical dissection in combination with effective suction, irrigation, coagulation, and cauterization that facilitates the performance of oropharyngeal surgery.

Another object of this invention is to avoid the risk of bleeding and to enhance healing by a dry, sharp dissection of any surgical procedure in the oropharyngeal cavity, especially tonsillectomy.

It is a further object of the present invention to provide an instrument that reduces operating time.

It is still a further object of the present invention to provide an instrument that reduces the number of instruments to set.

Another object of the present invention is to provide an instrument where little to no assistance is required from the scrub nurse during the surgical procedure, which frees the assistant to perform other tasks.

It is an object of the present invention to make oropharyngeal surgical procedures safer and simpler.

It is a further object of the present invention to provide an electrosurgical instrument that is cost effective, easy, and safe to use.

Still another object of the present invention is to provide an electrosurgical instrument which may be used by left-handed and right-handed surgeons alike.

Another object of the present invention is to provide an instrument which enables a surgeon to perform most of the surgical procedure using just one instrument.

Accordingly, it is a primary object of the present invention to overcome disadvantages of the prior art, such as the need for a multiplicity of devices and the required presence of ancillary personnel, among others, with an electrosurgical instrument capable of performing multiple functions.

The electrosurgical instrument itself, both as to its construction and its mode of operation, will be best understood, and additional objects and advantages thereof will become apparent from the following description of the preferred embodiments taken in conjunction with the accompanying drawings.

When the word "invention" is used in this specification, the word "invention" includes "inventions", that is, the plural of "invention". By stating "invention", the Applicant does not in any way admit that the present application does not include more than one patentably and non-obviously distinct invention, and Applicant maintains that the present application may include more than one patentably and non-obviously distinct invention. The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

FIG. 1 is a front view of the electrosurgical instrument of the present invention;

FIG. 2 is a front view of the electrosurgical instrument of the invention;

FIG. 3 is a detailed view of the serrated chiseled tip of the electrosurgical instrument of the invention;

DESCRIPTION OF THE PREFERRED EMBODIMENT

Referring now to the drawings, wherein like reference numerals designate the corresponding structure throughout the views, a multifunctional electrosurgical instrument 1 according to the present invention, as illustrated in FIGS. 1–3, comprises a serrated chisel tip 2 suitable for sharp, blunt or cutting dissections; a handle 3 with a proximal end 4, a distal end 5, and a dorsum 6; said handle's proximal end having a metal or plastic orifice disposed to be attached to an irrigation line 7, said handle's dorsum having a corrugated orifice 8 which increases its width to make easier the introduction of the suction tube of the operating room's vacuum system, and said handle's proximal end having a metal stick 9, isolated in approximately 60 percent of its surface, to be attached to the electrocauterizer's cable for cutting and coagulation, and a grooved area 10 where the suctioning intensity controls are located. This groove area has two orifices 11 reachable with the fingertips to control the intensity of the suction power. The instrument of the present invention can be formed of any suitable material, but the preferred embodiment is out of titanium, stainless steel or any other suitable long lasting light metal to facilitate the conduction of electricity in the electrocauterizer feature.

In turn, the metal instrument is coated with a suitable electrical isolation material such as PVC, rubber, or any other suitable isolation material, to avoid the leak of electricity to the surgeon or the patient avoiding an undesired burn.

In the preferred embodiment the electrosurgical instrument's handle is of octagonal or round shape for enhanced gripping in a stressful surgical environment. Nonetheless, other shapes may be possible without departing from the spirit and scope of this invention.

In the preferred embodiment, an irrigation tube is attached to a specially designed groove and ends at the tip in a chisel form to improve the aesthetic appearance of the instrument and the visibility of the tip area at the handle's dorsum.

In use, multifunctional electrosurgical instrument will normally be connected to a power source for electrocauterization through an electrocauterizer. The instrument can also be communicated with a source of suction to drain fluid from the operative site or with a source of irrigating fluid for supplying fluid to the operative site.

In the preferred embodiment, the instrument's length facilitates reaching any area in the oropharyngeal cavity.

The irrigation tube runs from the handle's dorsal, proximal portion of the tube to the tip in the distal portion. Such tube is attached at the handle's dorsum to a specially designed groove and ends at the tip, in a chisel form, to improve the aesthetics of the instrument and the visibility of the tip area.

More specifically, the present invention provides for use with a power source and is comprised of the following features: a serrated chisel tip for sharp, blunt or cutting dissection; an electrocauterizer, for coagulation of blood vessels or for use during cutting dissection; a variable speed suctioning feature to remove undesired blood in the surgical area, or to serve as irrigation source; and an irrigation feature, for ease in the identification of blood vessels and for removal of dangerous blood clots from the surgical area. A method of performing most oropharyngeal surgical procedures with a single instrument includes the steps of placing the serrated chisel tip at the distal end of a stainless steel, titanium or other long-lasting metal handle, in the surgical area; controlling the suctioning speed by reaching with fingertips two orifices embedded in grooved area of distal end; attaching an irrigation line through a metal or plastic orifice at the dorsum of the round or octagonal handle; and using a metal stick, isolated in 60% of its surface area, to be attached to the electrocauterizer's wire for coagulation and dissection effects.

An example of a multifunctional electrosurgical instrument which may be utilized or incorporated in at least one possible embodiment of the present invention may be found in U.S. Pat. No. 5,800,431 to Brown.

All of the patents, patent applications, and publications recited herein, and in the Declaration attached hereto, if any, are hereby incorporated by reference as if set forth in their entirety herein. The components disclosed in the various patents, patent applications, and publications, disclosed or incorporated by reference herein may be used in the embodiments of the present invention, as well as equivalents thereof.

All, or substantially all, of the components and methods of the various embodiments may be used with at least one embodiment or all of the embodiments, if more than one embodiment is described herein.

The details in the patents, patent applications, and publications may be considered to be incorporable at applicant's option, into the claims during prosecution as further limitations in the claims to patentably distinguish any amended claims from any applied prior art.

Thus, there has been shown and described a multifunctional electrosurgical instrument which fulfills all the objects and advantages sought therefor. Although only a few exemplary embodiments of this invention have been described in detail above, those skilled in the art will readily appreciate that many modifications are possible in the exemplary embodiments without materially departing from the novel teachings and advantages of this invention. For instance, the electrosurgical instrument of the present invention is designed for surgical procedures within the specialty of otorynolaryngology, head, and neck surgery. Nevertheless, smaller sizes designs may be used in endonasal or nasopharynx surgeries through endoscopes or oral cavity approach. In turn, the instrument of this invention, or an equivalent thereof, may be used in plastic surgery, neck surgery or surgery of extremities. Accordingly, all such modifications are intended to be included within the scope of this invention as defined in the following claims. In the claims, means-plus-function clauses are intended to cover the structures described herein as performing the recited function and not only structural equivalents but also equivalent structures.

What is claimed is:

1. An electrosurgical instrument, comprising:

a distal end and a proximal end;

means for dissection disposed at said instrument's distal end;

means for electrocauterizing;

means for suction of surgical field;

means for irrigation of surgical field;

a handle disposed at said instrument's proximal end, said handle having a proximal end, a distal end, and a dorsum, whereby an orifice is disposed to be attached to an irrigation line at the handle's proximal end, said handle having a slight groove area in said handle's distal end's sides, whereby two orifices are disposed in said groove area to facilitate contact with surgeon's fingertips, said handle's dorsum having an orifice disposed to be attached to a suction tube, and said handle's proximal end having a metal stick with isolation in approximately 60% of its surface, said metal stick disposed to be attached to an electrocauterizer's cable.

2. The electrosurgical instrument of claim 1, wherein said handle's dorsum is corrugated and tapered from the orifice located at said handle's dorsum to a wider size to facilitate the introduction of the suction tube.

3. The electrosurgical instrument of claim 2, wherein said instrument is made of a long lasting light metal.

4. The electrosurgical instrument of claim 3, wherein said metal instrument is coated with a suitable isolation material.

5. The electrosurgical instrument of claim 4, wherein the dissection means is a serrated chisel tip.

6. The electrosurgical instrument of claim 5, wherein the irrigation means is an irrigation tube housed within said instrument, said irrigation tube running from the handle's proximal end to said serrated chisel tip.

7. The electrosurgical instrument of claim 6, wherein said suction means is disposed within said serrated chisel tip.

8. The electrosurgical instrument of claim 7, wherein the instrument is of enough length to reach any surgical field in the oropharyngeal cavity.

9. The electrosurgical instrument of claim 8, wherein said handle is of round shape.

10. The electrosurgical instrument of claim 8, wherein said handle is of octagonal shape.

* * * * *